United States Patent [19]

Favre et al.

[11] 4,232,559
[45] Nov. 11, 1980

[54] METHOD AND AN APPARATUS FOR MEASURING THE BONDING POWER OF AN ADHESIVE MATERIAL

[75] Inventors: Jean-Paul Favre, Bourg la Reine; Joseph Perrin, Clamart; Michel Philbert, Paris; Jean Surget, Joinville le Pont, all of France

[73] Assignee: Office National d'Etudes et de Recherches Aerospatiales (ONERA), France

[21] Appl. No.: 48,255

[22] Filed: Jun. 13, 1979

[30] Foreign Application Priority Data

Jun. 15, 1978 [FR] France .................................. 78 17965

[51] Int. Cl.³ .............................................. G01N 3/08
[52] U.S. Cl. ..................................... 73/827; 73/150 A
[58] Field of Search ....................... 73/588, 827, 156 A

[56] References Cited

U.S. PATENT DOCUMENTS

| 3,527,093 | 9/1970 | Sellers | 73/150 |
|---|---|---|---|
| 3,945,248 | 3/1976 | West | 73/ |
| 4,184,373 | 1/1980 | Evans et al. | 73/588 |

Primary Examiner—S. Clement Swisher
Attorney, Agent, or Firm—Staas and Halsey

[57] ABSTRACT

A method for measuring the bonding power of an adhesive material, particularly a sheet material comprising fibres impregnated with a glue. After having applied against the material the face of a totally reflecting prism the index of refraction of which is lower than that of the glue, a force is exerted which tends to bring apart from each other the prism and said material, the value of the force corresponding to the separation is determined and the quotient is made of said force by the value of the contact area measured at the moment of the separation from the light totally reflected by said face.

10 Claims, 15 Drawing Figures

U.S. Patent Nov. 11, 1980 Sheet 1 of 4 4,232,559
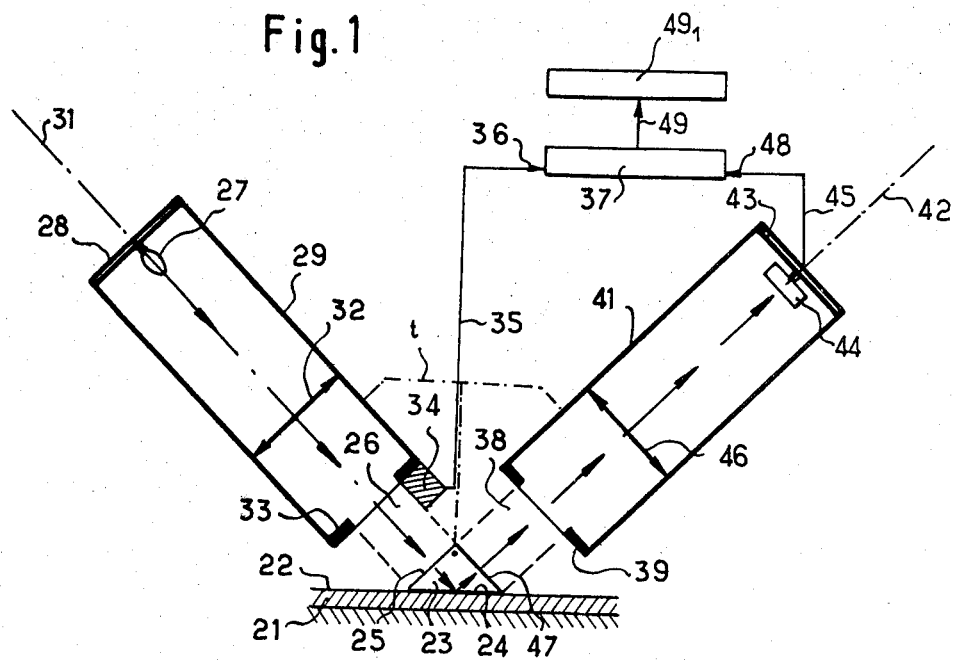
Fig.1
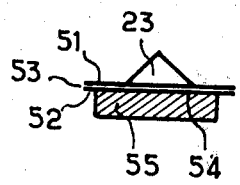
Fig.2
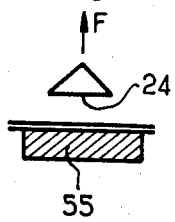
Fig.3
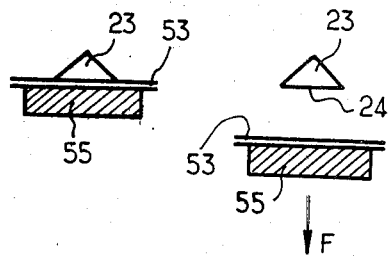
Fig.4
Fig.5
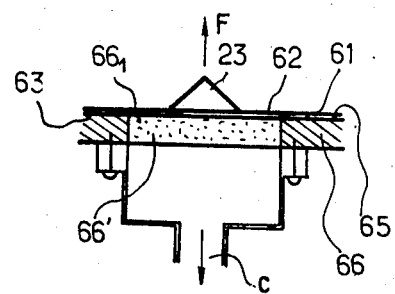
Fig.6

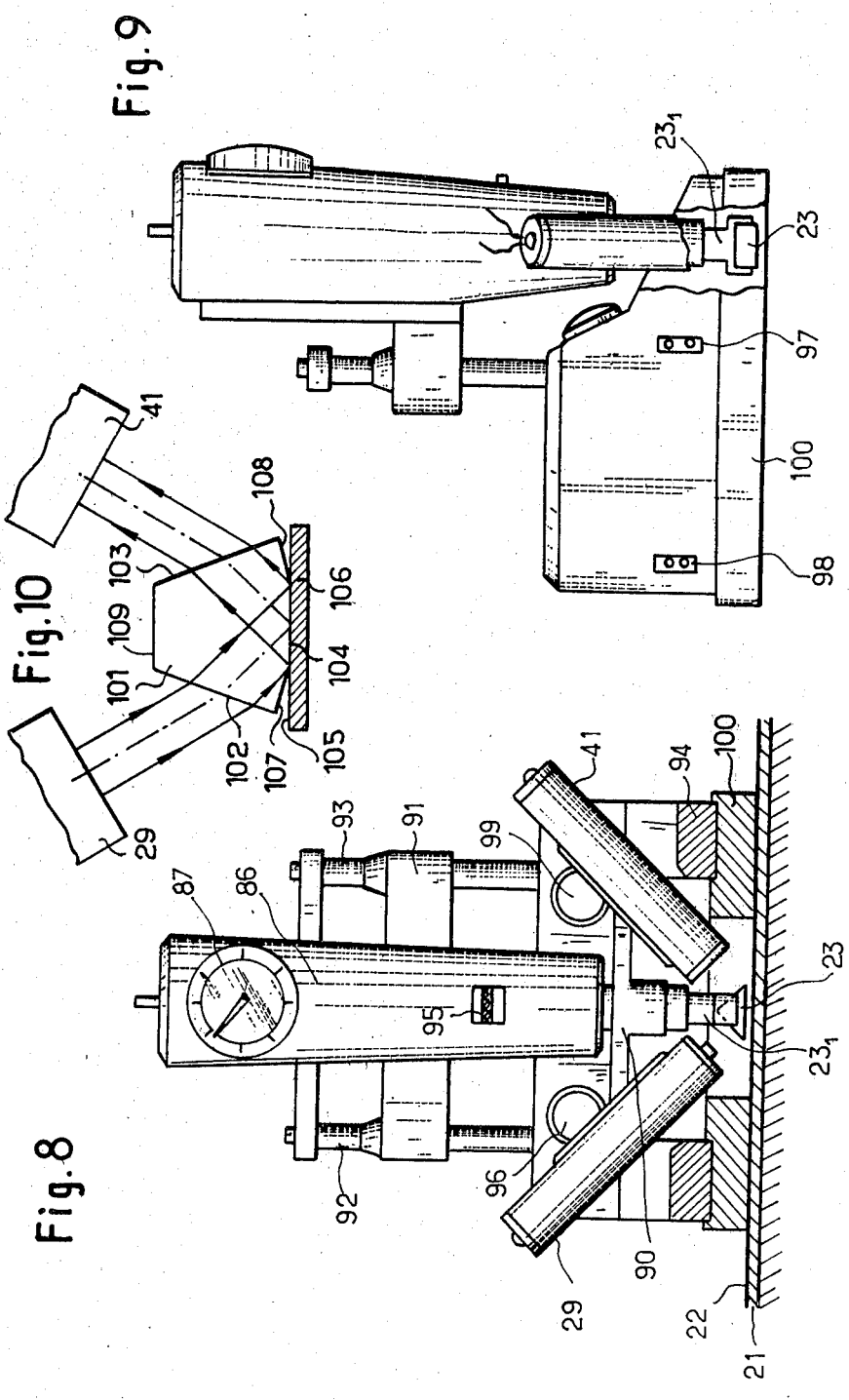

METHOD AND AN APPARATUS FOR MEASURING THE BONDING POWER OF AN ADHESIVE MATERIAL

The invention relates to a method and an apparatus for measuring an adhesion surface and the bonding power of an adhesive material.

Till now, for measuring the bonding power of an adhesive material, a reference surface of known area is brought in contact with said material, the reference surface being part of a member on which is then applied an increasing force perpendicular to the contact surface until the separation occurs. The bonding power is defined as being the ratio of the value of the force exerted when the separation occurs and of the contact area between the reference surface and the adhesive material.

While the value of the force can be known with precision through a dynamometric measurement, the information relative to the contact area is not accurate since the effective contact area is generally different from the nominal area, particularly in the case of heterogeneous adhesive materials such as those formed by resin impregnated fibres.

The invention fills in this gap.

It provides a method for determining the effective contact area of a reference surface with an adhesive material, and proposes to use as reference surface an optical element formed by a totally reflecting prism, the index of refraction of the prism being lower than that of the glue providing the adhesive material with its adhesiveness.

By directing a beam of parallel light rays perpendicularly to a face of the right angle of the prism, the reflection on the hypotenuse face is total since the latter has no contact with the adhesive or glue and, on the contrary, when part of the hypotenuse face is in contact with the glue having an index of refraction higher than that of the material forming the prism, a portion of the light is refracted and emerges from the prism through the hypotenuse face instead of being reflected by said face and coming out from the prism by the other face at right angle, so that the quantity of light coming out from the said other face of the right angle is a measure of the effective contact area between the hypotenuse face or reference surface and the adhesive material.

The invention provides a method for studying the bonding power of an adhesive material the adhesiveness of which results from the presence of a glue, wherein, after having applied on the adhesive material a totally reflecting optical prism having an index of refraction lower than that of the glue, after having directed perpendicularly to a face of the right angle of the prism a beam of parallel light rays and arranged a light captor on the beam due to the total reflection on the hypotenuse face of the prism, the totally reflecting prism is caused to be moved away from the adhesive material, the force exerted as well as the information supplied by the captor being measured in relation with time.

The knowledge of these two informations when the separation takes place provides the measurement of the bonding power of the adhesive material.

The invention is applicable to the measurement of the bonding power of an adhesive material on one face only as well as on both its faces.

It is also applicable in the rheology of adhesive materials, particularly formed by fibres imbedded in resin.

In the following description which is given by way of examplification, reference is being made to the accompanying drawings wherein:

FIG. 1 is a schematic view of an apparatus according to the invention;

FIGS. 2 to 6 are schematic views of various embodiments of the process according to the invention;

FIG. 8 is a frontal view of an apparatus according to the invention;

FIG. 9 is a corresponding side view;

FIG. 10 is a schematic view of an alternative embodiment; and

Figure 7:
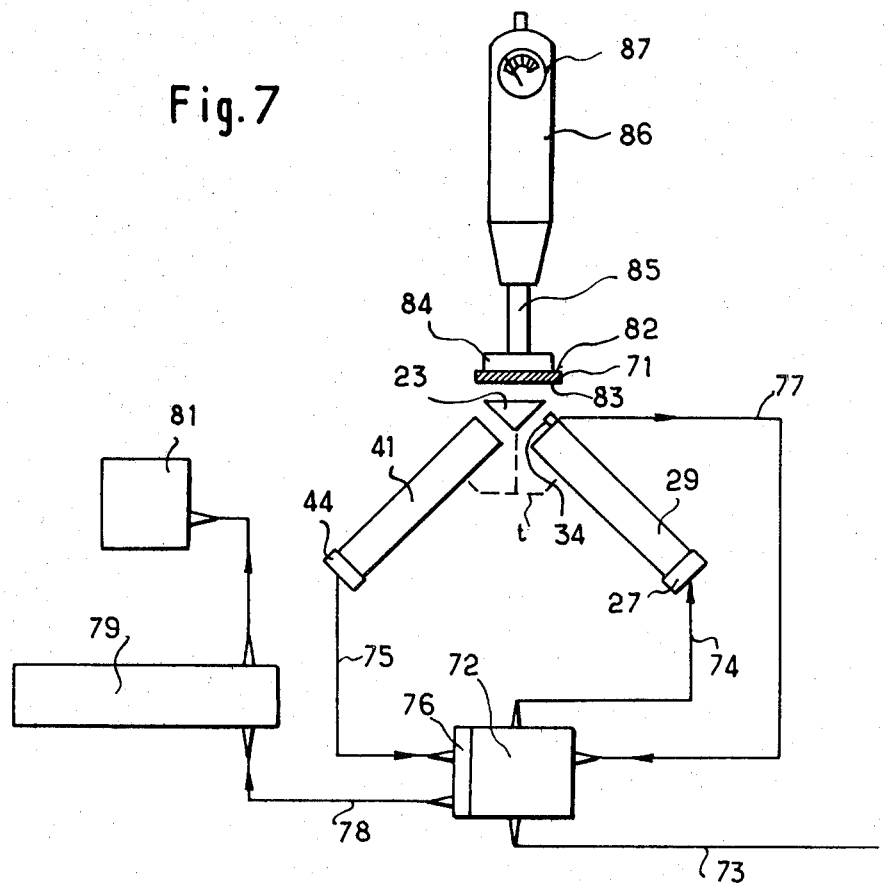
FIG. 7 is a schematic view of an installation for measuring the bonding power of an adhesive material.

Reference is first made to FIG. 1.

On a face 22 of an adhesive material 21 placed on a support, for instance a sheet material formed by braided fibres impregnated with a polyester type resin and used as a glue, is placed, by its hypotenuse face 24, a totally reflecting prism 23 formed by a bar of crown glass, having an index of refraction equal to 1.516, said index being lower than that of the glue whose index is equal to 1.565 in the case in consideration.

On a face 25 of the right angle of the prism 23 falls perpendicularly a beam 26 of parallel light rays supplied from a light source 27 placed on the bottom 28 of a tube 29, in the axis 31 of the latter. The light source 27 is advantageously an electroluminescent diode, means being provided for supplying the source 27 with a current modulated in amplitude. A lens device 32 inside the tube 29 supplies from the source 27 a beam of parallel rays emerging from the tube through a diaphragm 33. A portion of said beam is derived by means 34 comprising a photoelectric captor supplying an electrical voltage which, through a circuit 35, is applied to a first input 36 of a voltage comparator 37.

The beam 38 of parallel rays emerging from the totally reflecting prism 23 penetrates through a diaphragm 39 into a tube 41, in a parallel direction to axis 42 of the latter, on which is placed, at the bottom 43 of said tube which is opposite diaphragm 39, a photoelectric captor 44 supplying at its output 45 a voltage proportional to the light energy received, a lens device 46 focalizing the rays of beam 38 on captor 44. The voltage present at the output 35 is applied to the second input 48 of the comparator device 37.

The elements 29, 41 and the prism 23 are part of a rigid mechanical unit represented schematically by a chaindot line t.

When there is no contact between the hypotenuse face 24 of the totally reflecting prism 23 and the coating 22, all the light incident on the face 26 of the totally reflecting prism comes out through the perpendicular face 47 and the electrical voltage at the input 48 of the comparison device is maximum. The output 49 of the comparison device 37 transmits the voltage difference to a device $49_1$ formed by a digital voltmeter.

When there is a contact between the hypotenuse face 24 and the coating 22, the glue present on the contact area causes, due to its index of refraction which is higher than that of the material forming the prism 29, a light output by the hypotenuse face 24 so that the light energy incident on captor 44 decreases and the voltage at the input 48 decreases while that at the input 36 remains constant.

The comparison of the voltages at the inputs 36 and 48, displayed at $49_1$, is therefore an information on the effective contact area between the hypotenuse face 24 and the surface 22.

In order to measure the bonding power of an adhesive or glue, for example a resin, impregnating one or both faces, respectively 51 and 52 (FIGS. 2 and 3), of a composite sheet material 53 formed for instance by glass fibres impregnated with resin, said material is applied against the face, for instance the upper face 54 of a fixed support 55 by its face 52 and on the other face 51 of said material is applied a totally reflecting prism 23 which is part of an apparatus as described hereabove, the contact area between the face 52 and the support 55 being notably larger than the contact area between the hypotenuse face 24 of prism 23 and face 51. A mechanical action having a tendency to move away the sheet material 53 is exerted on prism 23. The condition shown in FIG. 3 is that where the force is sufficient for providing the separation of prism 23. The knowledge of the value F of said force and that of the effective contact area at the moment of the separation between the hypotenuse face 24 and the upper face 51 of the sheet material obtained as mentioned hereabove supplies, by a simple quotient, the accurate value of the bonding power of the material 53.

In the alternative embodiment shown in FIGS. 4 and 5, the mechanical action is applied not on the prism 23 but on the support 55, which is mobile, so as to tend to move away said support from the prism. The separation condition is shown in FIG. 5. In such a mode of execution, the prism 23 and the optical elements associated therewith remain fixed.

In the embodiment shown in FIG. 6, a sheet material 61 is coated with a glue on one only of its faces 62, the other face 63 being free from glue. A support 66, mobile, comprises a porous wall 66' the upper face 66₁ of which is flush with the upper face 65 of the support, the lower face of the porous wall being put in communication through a duct c with a vacuum pump. The action exerted by the vacuum is sufficient for preventing any movement of face 63 away from face 65.

By exerting a force F having a tendency of moving away the hypotenuse face 24 of the totally reflecting prism 23 from the adhesive face 62, the value of the force F when the separation occurs, compared to the value of the area measured by the apparatus shown in FIG. 1, provides the bonding power of the coating of the upper face 62.

Reference is now made to FIG. 7. In this embodiment, the apparatus for measuring the bonding power of the testpiece 71 comprises a current supply 72 connected to the mains 73 and a first output 74 which supplies the supply modulated current of the electroluminescent diode 27. The photoelectrical captor 44 is connected via a circuit 75 to the input of a voltage divider 76 connected via a circuit 77 to the device 34. The output 78 of divider 76 is connected to a voltmeter 79 which is in turn connected to a recording device 81.

The test-piece 71 is rigidly connected by its face 82 which is opposite its glued face 83 to a contact stud 84 carried by the stem 85 of a dynamometer 86 on the dial 87 of which can be read at any moment the force exerted.

The apparatus according to the invention may be realized in portable form, of small mass and occypying a small space. Such an embodiment is shown in FIGS. 8 and 9. This embodiment comprises the essential elements of the embodiments shown in FIGS. 1 and 7. The prism 23 is carried on a fork 23₁ surrounding it by its end faces. The tubes 29 and 41 are fixed on the support 90, which is itself rigidly connected to a tubular body 86 carrying the dynamometer 87. The tubular body 86 is rigidly connected to a bracket 91 sliding on two columns 92 and 93 fixed on the stand 94 of the apparatus.

The vertical movement of the bracket 91 is provided by an electrical motor housed inside the stand 94, through a tangent wheel and an endless screw, not visible in the figures, and by means of which one may control the bringing in contact of prism 23 with the adhesive surface 22, and then control a movement in the reverse direction developping the force having a tendency to separate the prism from the adhesive surface, the forces exerted being displayed on the dynamometer 87 dial.

The dynamometer comprises auxiliary means 95 for setting the limit force to be exerted and the adjustment of its needle.

The stand 94 of the apparatus contains the current supply 72 and the comparator 37. It lies on a base 100 of a non adhesive material such as for instance teflon.

Reference 96 indicates a starting switch and reference 97 the connecting socket to the mains. Reference 98 indicates the measuring output towards the votlmeter 79 and the recording apparatus 81. Reference 99 indicates the setting means of the signal supplied by the voltage comparator. When the prism 23 is not applied on the adhesive surface 22, the signal corresponds to 100% of the light transmitted by the prism.

With the apparatus according to the invention, it is possible to study the evolution as a function of time of the contact surface of a reference surface applied on an adhesive material.

In FIG. 10 is shown schematically a portion of an apparatus comprising a totally reflecting prism 101 the respective input and output faces 102 and 103 of which form an angle of 60°, the face 104 which is applied against the face 105 of the sheet 106 in adhesive material being connected to faces 102 and 103 by oblique faces 107 and 108, the prism being truncated by a face 109. Thus is reduced the space in width occupied by the apparatus.

Figure 11:
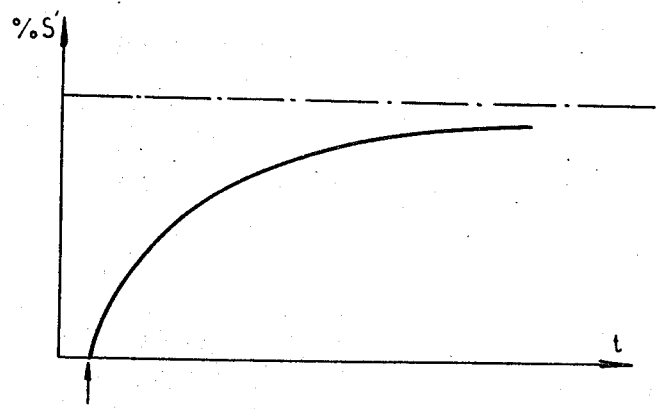
FIGS. 11 to 15 are diagrams.

FIG. 11 shows a curve obtained by appluing prism 23 on the adhesive surface and by recording the voltage supplied by the comparator and measured by the voltmeter. It supplies at each moment the percentage of the contact area S relative to the nominal area S' formed by the hypotenuse face of prism 23. As expressed in log. of t, the function is linear.

Figure 12:
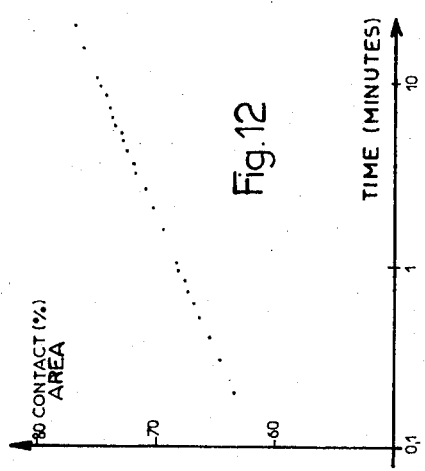
Figure 15:
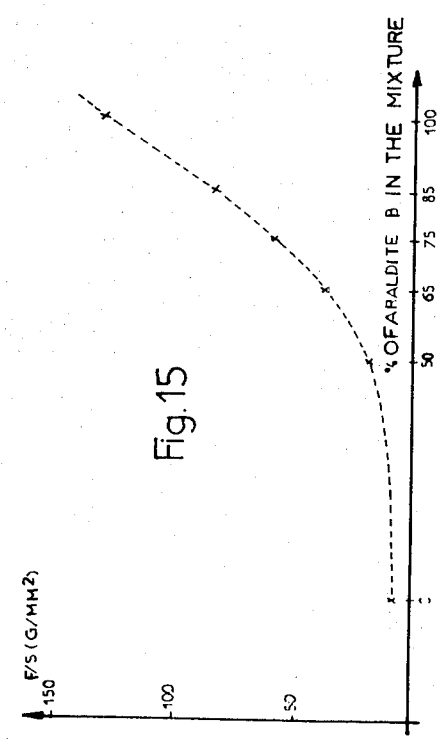

FIG. 12 is a curve showing the evolution of the contact surface as a function of time, plotted for a double face adhesive material known under the name of "SCOTCH" on which is applied the prism with a force of 1 kg.

Figure 13:
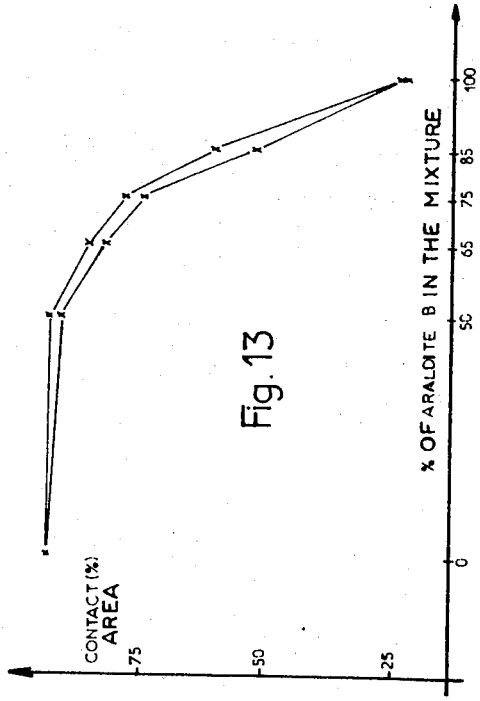

FIG. 13 shows the value of the contact surfaces obtained on a material formed by a glass fabric impregnated with an epoxy resin comprising an araldite liquid resin of the F type and a very viscous resin of the B type, mixed in a proportion of 0, 50, 65, 75, 85 and 100% by weight of solid resin in the mixture.

The fabric is available in the trade under reference 664 manufactured by the BROCHIER Company. It is impregnated with 45% by weight of araldite F and araldite B mixed in the proportions mentioned.

For each of these mixtures, the prism has been applied with a force of 1 kg for one minute and the percentage of contact surface has been recorded. The area delimited by the streight lines joining the crosses corresponding to the test points show the dispersion of the measurements for six identical measurements made relative to each of the mixtures.

One will remark on the figure the low dispersion obtained.

With the apparatus of the invention, one can therefore measure the bonding power of an adhesive material.

Figure 14:
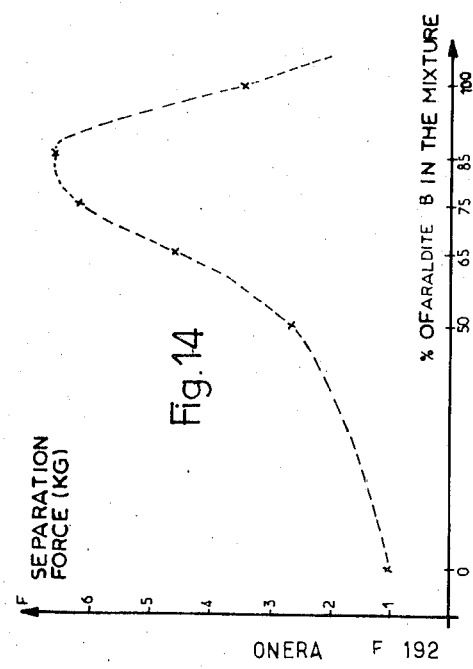

FIG. 14 is a diagram representing the separation force exerted on the pre-impregnated material described with reference to FIG. 12, similarly impregnated with a resin mixture in the same proportions.

For each of the test points, the prism has been applied with a load of 1 kg for one minute, then a force has been exerted for obtaining the separation and the force has been measured when the separation has taken place.

FIG. 14 shows the variation of the bonding power relating to the aforementioned impregnated material.

We claim:

1. A method for measuring the bonding power of an adhesive material, particularly a sheet material comprising fibres impregnated with a glue, wherein, after having applied against the material the face of a totally reflecting prism the index of refraction of which is lower than that of the glue, a force is exerted which tends to bring apart from each other the prism and said material, the value of the force corresponding to the separation is determined and the quotient is made of said force by the value of the contact area measured at the moment of the separation from the light totally reflected by said face.

2. A method according to claim 1, wherein the proportion of totally reflected light is measured relative to the light entering into the prism.

3. A method according to claim 1, wherein the force tending to the separation is exerted on the prism.

4. A method according to claim 2, usable for a sheet material with two adhesive faces, wherein on its face opposite that where the prism is received, the material is applied on a support on an area notably superior to that of the hypotenuse face of the prism.

5. A method according to claim 4, wherein the force tending to the separation is applied to the support.

6. A method according to claim 1, for the measurement of the bonding power of a material adhesive on one face only, wherein said material is, by its other face, applied on a support by a pneumatic depression of higher value than that of the separation force.

7. A method according to claim 6, wherein the support is porous.

8. An installation for practicing the method according to any one of claims 1 to 7, characterized in that it comprises an apparatus including a totally reflecting prism, means for directing on one of the side faces of the prism other than the totally reflecting face a beam of parallel rays perpendicular to said side face and means for comparing the quantity of incident light with the quantity of light emerging from the other side face of the prism, means for tending to bring away the totally reflecting face of the prism from the cooperating face of the material, means for permanently noting the intensity of the force tending to cause said movement away.

9. A totally reflecting prism apparatus as in included in the installation according to claim 8.

10. An apparatus according to claim 9, characterized in that it comprises means for deriving a portion of the incident light in view of the comparison.

* * * * *